(12) United States Patent
Capocchi et al.

(10) Patent No.: US 8,128,909 B2
(45) Date of Patent: Mar. 6, 2012

(54) PREPARATION OF STERILE AQUEOUS SUSPENSIONS COMPRISING MICRONISED CRYSTALLINE ACTIVE INGREDIENTS FOR INHALATION

(75) Inventors: Andrea Capocchi, Parma (IT); Fausto Pivetti, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 1144 days.

(21) Appl. No.: 10/538,888

(22) PCT Filed: Dec. 17, 2003

(86) PCT No.: PCT/EP03/14386
§ 371 (c)(1),
(2), (4) Date: Apr. 14, 2006

(87) PCT Pub. No.: WO2004/054545
PCT Pub. Date: Jul. 1, 2004

(65) Prior Publication Data
US 2007/0140980 A1    Jun. 21, 2007

(30) Foreign Application Priority Data

Dec. 18, 2002 (IT) ............................. MI2002A2674

(51) Int. Cl.
*A61K 9/14* (2006.01)
*A61K 9/72* (2006.01)
*A61K 31/573* (2006.01)
*A61L 2/02* (2006.01)
*A61K 9/00* (2006.01)

(52) U.S. Cl. .......... 424/43; 424/400; 424/489; 514/180; 514/826; 514/937; 514/951; 514/958; 422/1

(58) Field of Classification Search ....................... None
See application file for complete search history.

(56) References Cited

U.S. PATENT DOCUMENTS

| 6,187,765 | B1 * | 2/2001 | Harris et al. ................... 514/172 |
| 6,241,969 | B1 * | 6/2001 | Saidi et al. ...................... 424/45 |
| 6,464,958 | B1 * | 10/2002 | Bernini et al. .................. 424/43 |
| 2005/0222108 | A1 | 10/2005 | Bhatarah et al. | |

FOREIGN PATENT DOCUMENTS

| GB | 2 107 715 | | 5/1983 |
| GB | 2107715 | A * | 5/1983 |
| WO | 99/53901 | | 10/1999 |
| WO | 00/25746 | | 5/2000 |
| WO | 02/00198 | | 1/2002 |
| WO | 02/00199 | | 1/2002 |
| WO | WO 0200199 | A1 * | 1/2002 |

* cited by examiner

*Primary Examiner* — Ernst Arnold
*Assistant Examiner* — Christopher R Lea
(74) *Attorney, Agent, or Firm* — Oblon, Spivak, McClelland, Maier & Neustadt, L.L.P.

(57) ABSTRACT

Disclosed is a process for the preparation of sterile aqueous suspensions based on active ingredients in the form of micronised crystalline particles designed for administration by inhalation. In particular, a process for the preparation of sterile aqueous suspensions based on pharmaceutical active ingredients in the form of crystalline hydrates is disclosed.

14 Claims, 2 Drawing Sheets

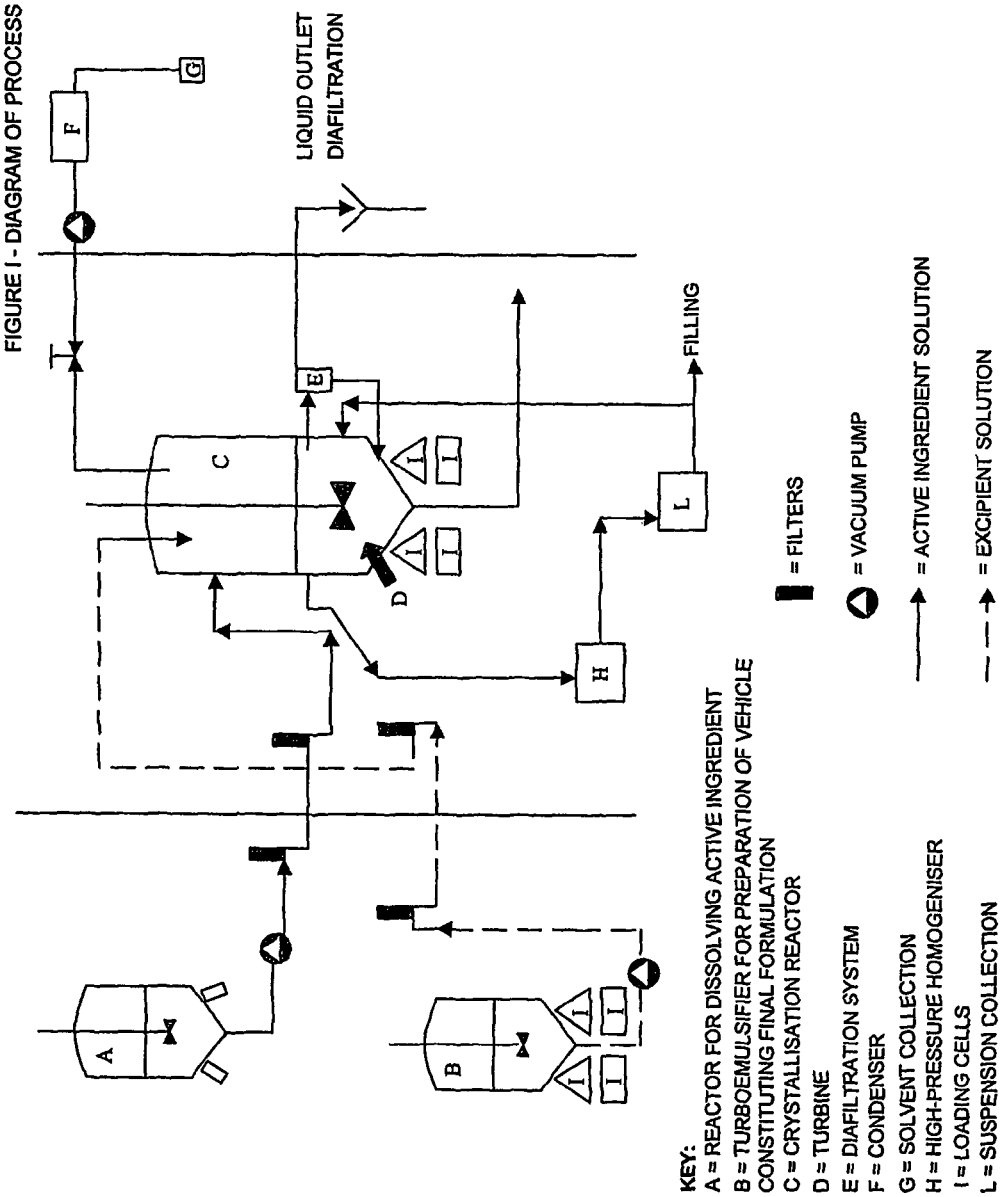

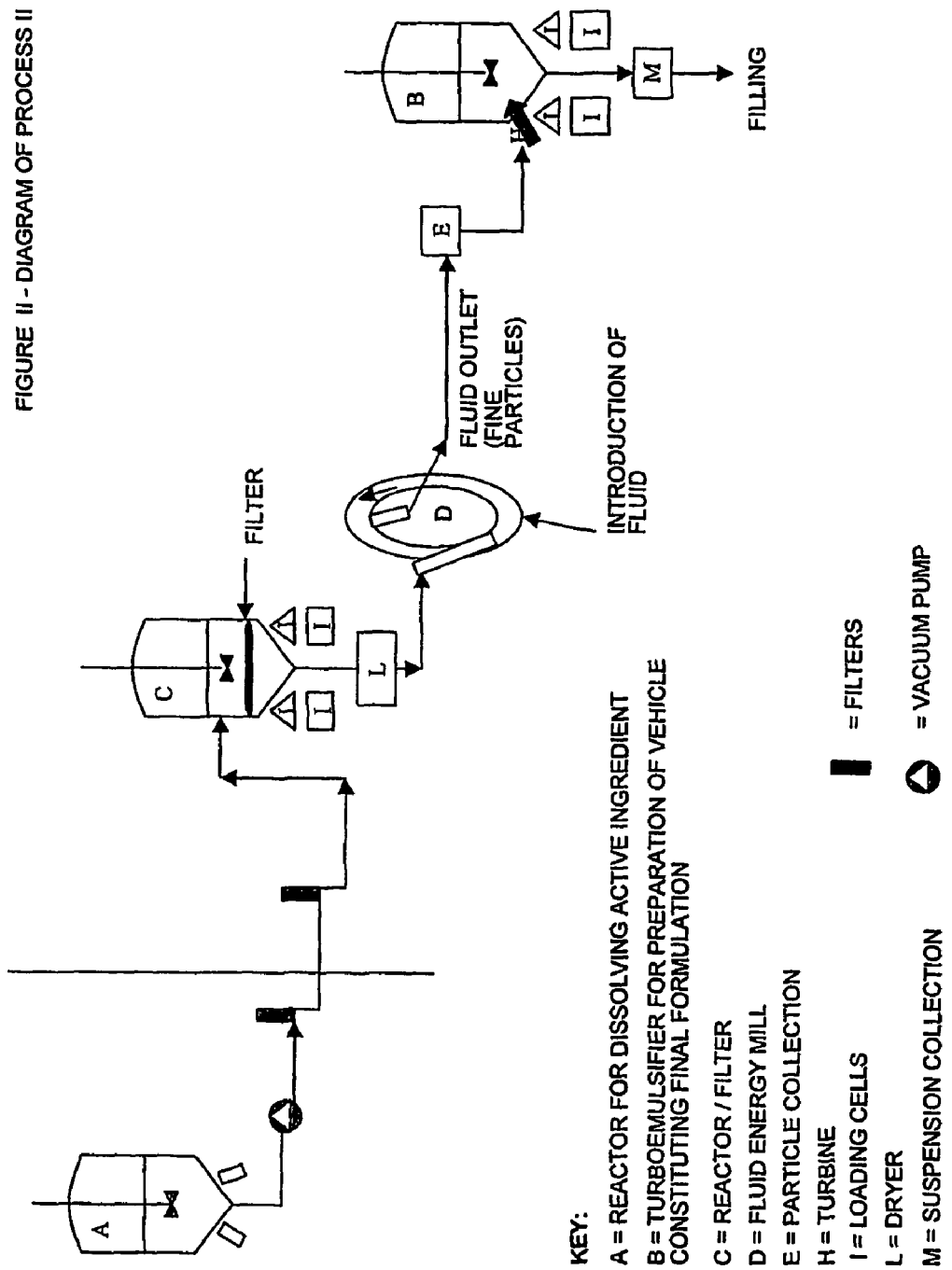

PREPARATION OF STERILE AQUEOUS SUSPENSIONS COMPRISING MICRONISED CRYSTALLINE ACTIVE INGREDIENTS FOR INHALATION

This invention relates to a process for the preparation of sterile aqueous suspensions based on micronized crystalline active ingredients designed for delivery by inhalation.

BACKGROUND OF THE INVENTION

The method of delivering drugs by inhalation has been used for several years, and is the mainstay of the treatment of disorders which limit the respiratory flow, such as asthma and chronic bronchitis.

The advantages of inhalation over the systemic route include the fact that the drug is released directly at the site of action, thus preventing systemic side effects and resulting in a faster clinical response and a higher therapeutic index.

These advantages have also been used in the pulmonary administration of drugs designed to produce a systemic effect in the treatment of non-pulmonary disorders. Drugs administered by the inhalation route are dispensed in the form of powders by powder inhalers, as solutions or suspensions in fluorinated propellant by pressurized metered dose inhalers (MDI), or as aqueous solutions or suspensions by suitable ultrasound or compressed-air nebulisers. These drugs belong to different therapeutic classes: they are represented in particular by drugs designed for the treatment of respiratory diseases, such as antibiotics, corticosteroids, mucosecretolytics, anticholinergics and β2-adrenergic receptor agonists.

The aerosol therapy is mainly used to treat inflammatory disorders; in this field, a special place is held by corticosteroids such as beclomethasone dipropionate (BDP), mometasone furoate, flunisolide, budesonide, ciclesonide and fluticasone propionate. These drugs are generally administered in micronised form in suspension in an aqueous vehicle or in a propellant. The drug is inhaled in aerosol form, i.e. in the form of a dispersion of solid particles in a gaseous medium. The efficacy of this form of administration depends on the deposit of a sufficient amount of particles at the site of action.

If peripheral areas of the respiratory tree, such as the alveoli, are to be reached, as in the case of bronchopulmonary formulations, one of the most important parameters is the particle size, which must be lower than or equal to 5-6 micron. This size is quantified by measuring a characteristic sphere-equivalent diameter, known as the median aerodynamic diameter (MAD), which expresses the ability of particles to be transported in suspension in an airstream. Another parameter widely utilised is the mass median aerodynamic diameter (MMAD) which corresponds to the MAD of the 50 percent by weight of the particles.

Particles with a larger MAD are ineffective, because they are deposited in the oropharyngeal cavity, and are therefore unable to reach the terminal branches of the respiratory tree. They can also give rise to local side effects, or may be absorbed through the mucous membranes and give rise to systemic side effects.

Particles of suitable size for inhalation treatment are not generally obtainable by simple crystallisation from a solution. In order to obtain high crystallinity and adequate purity, and to minimise the residual solvent content, products for pharmaceutical use are crystallised slowly; however, particles with a non-uniform size which exceeds the upper limit specified above are normally produced under these conditions. On the other hand, in order to obtain a fine precipitate, the crystallisation process must be rapid but in this case it is very difficult to identify the relevant parameters such as solvent, concentration, temperature and time, so as to obtain a completely crystalline product and/or avoid the inclusion of impurities in the crystals. Products designed for inhalation therefore normally undergo a micronization treatment. This treatment is usually performed in a fluid energy mill constituted by a chamber with a circular or other geometrical shape (e.g. a flattened ring), with a lateral extension into which the active ingredient to be micronised is introduced. A fluid, generally air or nitrogen, is injected at high pressure through nozzles in the bottom of the unit. The solid material is introduced into the fluid stream, and as a result of the high turbulence created, develops friction and impact between particles and between the particles and the chamber walls, which leads to a reduction in their size. A centrifugal classifier (cyclone) is incorporated into the apparatus so that the particles are retained until they reach the desired degree of fineness. Solid materials, especially steroids, usually contain particles with sizes of up to 150 micron before being micronised. In order to obtain particles of suitable dimensions for pulmonary administration (5-6 micron), the parameters involved (fluid pressure, chamber temperature, time of solid material addition and micronization time) must be regulated on the basis of the characteristics of the active ingredient (initial size, and hardness of crystal). In general, the larger their size and the harder the crystal, the more time the particles must remain in the micronization chamber, and/or the higher the flow rate and pressure of the fluid used need to be. The micronization of steroids such as BDP is usually conducted at a pressure of between 10 and 12 bar, for approx. 30 minutes.

However, micronization techniques have some drawbacks, including the fact that the percentage of particles obtained having the desired particle size may be relatively small. The yield of the process can also be relatively low (considerable loss of product can be caused by its adherence to the walls of the apparatus used). Another disadvantage is that in the case of solvated products, the conditions used can cause loss of solvent, with a change in the crystalline structure and consequent formation of polymorphs. Another undesirable characteristic of micronised products is that the surface of the particles generated is often mainly amorphous, so that they tend with time to be converted into the more stable crystalline state, which may be different from the original state. The harder the conditions and the longer the micronization time, the greater the degree of amorphization. This drawback is particularly significant in the case of active ingredients which need to be resuspended in water. Materials which are even only partly amorphous are more liable than crystalline materials to moisture uptake (Hancock et al. *J. Pharm. Sci.* 1997, 86, 1-12), and this has adverse effects on active ingredients whose chemical stability is particularly sensitive to the humidity content.

Another drawback of micronization processes is that they require high energy and therefore require containment and other measures to avoid the risk of explosion.

Another problem which may affect micronised products, when formulated as suspensions, is an increment of the particle size over time as a result of total or partial recrystallisation of the small quantity of dissolved solute (Davis et al *Int J Pharm* 1, 303-314, 1978; Tiano et al *Pharm Dev Tech* 1, 261-268, 1996; Taylor et al *Int J Pharm* 153, 93-104, 1997). Such an increase can prejudice the efficacy of nebulisation and therapeutic efficacy because, as stated, particles with an MAD exceeding 5-6 µm are unable to reach the preferential site of action.

The phenomenon of 'crystalline growth' has been observed in particular for some steroids, such as BDP and flunisolide.

When these active ingredients are formulated in suspension in inhaler propellants or aqueous vehicles, the crystals grow, leading to the formation of particles with a greater particle-size distribution than the original one. Another important requirement that must be met by pharmaceutical formulations designed for pulmonary delivery is sterility. This requirement is more and more recommended in various documents dealing with quality and safety of pharmaceutical products for a number of reasons, including the fact that the lungs are a particularly vulnerable organ of the human body, and many patients who use inhaled drugs have general health problems. The current trend is to produce inhalation formulations devoid of preservatives and bacteriostatics, as it has been reported in the literature that some of the substances commonly used for this purpose can give rise to allergic reactions or irritate the respiratory mucosae (Menendez R et al *J Allergy Clin Immunol* 84, 272-274, 1989; Afferty P et al *Thorax* 43, 446-450, 1988). Various processes can be used to manufacture sterile pharmaceutical formulations for inhalation. For example, the active ingredient can be pre-sterilised by dry heating or radiation, followed by preparation of the formulation under aseptic conditions as reported in WO 99/25359 and WO 00/25746, or the formulation can be pre-prepared and sterilised by treatment in an autoclave.

However, all the sterilisation methods reported for aqueous suspensions suffer from drawbacks or limitations. For example, pre-sterilisation methods require a subsequent stage of mixing of the active ingredient thus obtained with the other ingredients of the formulation, and preparation of the final formulation under aseptic conditions till the introduction into the final sterile container. Standard autoclaving treatments are unsuitable for aqueous suspensions of thermolabile corticosteroids (such as BDP), because they cause the chemical degradation of the active ingredient. These treatments can also give rise to agglomerates of particles of the active ingredient in the suspension which are difficult to redisperse, thus jeopardizing their therapeutic efficacy. Finally, in the case of suspensions, sterilizing filtration is not feasible because it requires the use of filters with a pore size less than or approximately equal to 0.2 micron, not compatible with the size of the disperded particles.

Various prior publications specifically refer to processes for obtaining active ingredients for pulmonary administration in a crystalline form by crystallisation from a solution in a suitable solvent upon addition of a proper anti-solvent.

GB 2107715, filed by Glaxo, describes the preparation of BDP monohydrate for use in the preparation of pharmaceutical compositions in dry powder form. The text states that BDP monohydrate can be prepared by crystallisation by slowly adding a solution of BDP in a water-miscible organic solvent, which may be ethanol, to water. After crystallization, the monohydrate may be isolated by, for example, filtration and washed and dried in conventional manner. The beclomethasone dipropionate monohydrate is then micronized to the desired particle size range by conventional techniques, for example using a ball mill or fluid energy mill or by ultrasonic means.

At least 90% in weight of the particles obtained are under 10 micron in size, and preferably 2-5 micron. The active ingredient is then formulated as a dry powder in a mixture with conventional solid diluents.

There is no teaching about how to make a sterile crystalline BDP monohydrate and/or pharmaceutical compositions in form of aqueous suspension for pulmonary delivery wherein the particle size distribution of the crystalline active ingredient does not change.

In the prior art, BDP monohydrate was only used to prepare suspensions in fluorinated propellants, to be delivered by metered dose inhalers, which do not need to be sterilised (patent applications WO 93/15741, WO 96 32345 and WO 99/53901 filed by Glaxo). Otherwise, BDP monohydrate has been used to prepare aqueous suspensions for nasal administration which are not sterile, and in order to be effective at the nasal mucosa level normally contain particles with a MAD greater than 10-20 micron, as proposed in the FDA guideline "Bioavailability and Bioequivalence Studies for Nasal Aerosols and Nasal Sprays for Local Action" issued in June 1999.

WO 90/03782, filed by the Upjohn Company, describes a process for the preparation of finely divided solids which involves dissolving the solid in a suitable solvent and adding the solution to an anti-solvent chosen from the group of supercritical fluids, compressed gases or condensed vapours. The preferred anti-solvent is carbon dioxide, while the solvent should be chosen according to the type of active ingredient.

U.S. Pat. No. 5,314,506, filed by Merck, claims a process for crystallisation of an organic pharmaceutical compound which comprises contacting one or more jet streams of a feed solution of the compound with one or more jet streams of an anti-solvent in conditions of high turbulence and with sufficient linear velocity to produce crystals with a diameter equal to or less than 25 micron. One of the jet streams optionally includes a surfactant, to prevent agglomeration of the particles.

WO 96/32095, filed by Astra, discloses a process for producing a pharmaceutical powder for inhalation with crystalline particles having a diameter of less than 10 micron which involves preparing a saturated or supersaturated solution of active ingredient and causing it to collide, in the form of a jet stream or droplets obtained through a nozzle or porous filter, with an anti-solvent under agitation. Methanol, isopropanol, dimethylsulphoxide, dimethylformamide and others can be used as organic solvents in the case of water-insoluble active ingredients. The text states that the process preferably takes place at a low temperature (below 25° C., and preferably between 0 and 5° C.). The examples refer to budesonide.

U.S. Pat. No. 5,314,506 and WO 96/32095 require isolation of the products before preparation of the final formulation, and are therefore incompatible with a continuous production process. The applicant has also demonstrated that due to the Venturi effect, the delivery of a solution as a spray through a nozzle leads to cooling of the organic solution, which in turn can cause crystallisation of the active ingredient and clogging of the nozzle under supersaturated conditions.

In WO 00/25746, filed by the applicant, aqueous suspensions for nebulisation based on a micronised steroid designed for inhalation, sterilised with gamma rays are described. The process basically involves a first stage of preparation in a turboemulsifier of an aqueous solution which constitutes the vehicle and contains suitable excipients, followed by the addition of the sterile micronised active ingredient and its dispersion at atmospheric pressure in the same turboemulsifier. The dispersion of the active ingredient in the aqueous phase may be subjected to an additional high-pressure homogenising treatment which further reduces the average size of the particles in suspension. The examples refer to BDP.

WO 01/49263, filed by Orion, relates to a process which involves: i) preparing a solution or suspension of active ingredient; ii) atomizing it to create droplets; iii) suspending said droplets in an inert gas which acts as carrier gas; iv) passing them through a heated tube flow reactor; v) collecting the particles with conventional techniques.

The invention is designed for active ingredients delivered by inhalation, with crystalline, spherical, rough, uncharged particles. This process is incompatible with a continuous production process. The passage through a tube flow reactor also involves a heating stage, which may not be compatible with thermolabile substances such as some steroids designed for inhalation.

WO 00/53282, filed by Smithkline Beecham, discloses a process for the continuous crystallisation of an organic compound which involves contacting a solution of active ingredient with an anti-solvent or colder solvent, or a suitable solution of an acid or base, and separating the crystals formed. The process preferably takes place in conditions of turbulence, and precipitation preferably takes place in less than 1 minute, and even more preferably in less than 5 seconds. The examples relate to eprosartan methanesulphate and nabumetone, two active ingredients unsuitable for administration by inhalation. For the former, the preferred solvent is acetic acid and the preferred anti-solvent is tert-butyl methyl ether or ethyl acetate. For the second active ingredient, the preferred solvent is 2-propanol, and the preferred anti-solvent is water.

WO 01/14036, filed by Aventis, claims a method for the preparation of drug particles which involves: i) dissolving the active ingredient in a solvent; ii) collision with an anti-solvent under conditions of turbulence followed by rapid precipitation of the active ingredient in the form of crystalline particles with a controlled diameter. This process is characterised in that the velocity of the opposing streams must exceed 50 m/sec, the ratio between anti-solvent volume and solvent volume must be >2:1 (preferably between 15:1 and 30:1), and the angle of collision between the two streams must preferably be less than 20 degrees. The invention is designed to produce drugs for inhalation with a final diameter of between 2 and 5 micron. Triamcinolone acetonide is indicated as the preferred active ingredient. There is no teaching relating to obtaining a sterile product, and in any event the process is incompatible with a continuous production process.

Various patent applications filed by Glaxo (WO 00/38811, WO 01/32125, WO 02/00198 and WO 02/00199) relate to processes for the preparation of crystalline particles of a substance which comprises the following stages: i) mixing a solution of active ingredient with an anti-solvent in a continuous-flow cell to generate a suspension; ii) filtering the suspension so as to isolate the particles with a diameter of between 1 and 10 micron, and preferably under 5 micron; iii) isolating and collecting the particles using techniques such as freeze-drying. In particular, the applications relate to conditions of isolation of the products (and consequently elimination of the solvents) which prevent crystalline growth of the particles during the isolation process.

The examples refer to fluticasone and salmeterol.

In WO 00/38811 and WO 02/00199 it is expressly stated that when the active ingredient is BDP, industrial methylated spirits (IMS) will preferably be used as organic solvent.

Here again, unlike the present invention, the processes always involve isolation of the products before preparation of the final formulation, and are therefore incompatible with a continuous production process.

In view of all these drawbacks, it would be a great advantage to provide a process which overcomes or at least mitigates the limitations of the technical solutions proposed in the prior publications.

SUMMARY OF THE INVENTION

A process for the preparation of sterile aqueous suspensions for nebulisation, which comprise a micronised active ingredient insoluble in water, has now been found. Said process comprises the following steps
i) a solution of the active ingredient in an organic solvent is prepared in a suitable reactor (A);
ii) said solution is sterilised by filtration;
iii) in parallel, a sterile aqueous phase containing pharmaceutically acceptable excipients is prepared in a turboemulsifier (B);
iv) the sterile organic solution ii) is added in a suitable reactor (C) to the sterile aqueous phase iii) to yield the active ingredient in crystalline form so forming a sterile suspension;
v) the organic solvent is eliminated;
vi) the suspension is filled in suitable containers under sterile conditions.

The temperature of the organic solution is preferably between 25 and 80° C., preferably between 40 and 70° C., and that of the sterile aqueous phase between 5 and 50° C., preferably between 10 and 25° C.

One of the advantages of the process according to the invention is that the active ingredient is sterilised by simple filtration through sterilizing filters avoiding heating or irradiation.

A further advantage is that said process can produce particles with a controlled particle size distribution, preferably with a MMAD lower than 6 micron which is suitable for products administered by pulmonary inhalation.

Moreover, the process of the invention allows continuous processing without separation of the intermediate products; all stages of the process take place at room temperature, can be conducted without contact with air, and are therefore compatible with manufacture in aseptic conditions.

Hereafter, the term "solvent" is used to mean the medium in which the active ingredient is dissolved, and "anti-solvent" to mean the medium in which its precipitation takes place, and which determines the crystalline characteristics of the product.

The anti-solvent of the present invention is always water.

As excipients, pharmaceutically acceptable ingredients commonly used for the preparation of aqueous suspension formulation are used. In particular, it is preferable for wetting agents to be present in the water that acts as anti-solvent.

It has been found that the presence of wetting agents at the crystallisation stage promotes the formation of the hydrated form of particular kinds of active ingredients, namely a physically stable form which does not give rise to crystalline growth once in suspension in water, without altering their characteristics of purity and the degree of crystallinity.

In a particular embodiment of the invention the active ingredient is further subjected to a wet micronization treatment in a high-pressure omogeneizer (H), without prior isolation of the product, to give rise to an even better distribution of the particle size of the active ingredient, with a MMAD lower than or equal to 3 to 4 micron. Said treatment is not only bland, but also eliminates the problems associated with dry micronization, as the particles are uniformly dispersed in the aqueous vehicle.

The process of the invention can also envision isolation and collection of the active ingredient particles, after addition of the anti-solvent to the organic solution in reactor (C), by filtration under sterile conditions, followed by a reduction in the particle size of the active ingredient by dry micronization in a fluid energy mill (D) operating in a sterile environment.

The micronised active ingredient thus obtained is then dispersed in a turboemulsifier (B) in which a pre-sterilised aqueous solution containing the excipients has been prepared. The filling in suitable container under sterile conditions completes the process.

In fact, it has been found that the particles of active ingredient, obtained after addition of the anti-solvent according to the process of the invention, can easily be isolated by filtration under sterile conditions without clogging the filter. Said particles, by virtue of their particle-size distribution, can be micronised in the fluid energy mill at lower operating pressures (5-6 bar) than those normally used (10-12 bar) that could prejudice or alter their crystalline state. The use of bland conditions also allows to reduce the flow rate of the high-pressure fluid (sterile air or nitrogen), thereby lowering the costs.

A further aspect of the present invention relates to aqueous suspensions of micronised crystalline active ingredients obtained with the claimed process, for delivery by inhalation. Particularly preferred are sterile formulations in the form of aqueous suspensions designed for pulmonary delivery of corticosteroids for the treatment of respiratory disorders such as asthma and chronic bronchitis.

An even more preferred sterile formulation comprises crystalline particles of BDP monohydrate wherein the volumetric diameter of at least 90% of the suspended particles is less than or equal to 10 micron, preferably 8 micron, more preferably 6 micron.

DETAILED DESCRIPTION OF THE INVENTION

The characteristics of the process and the pharmaceutical compositions of the invention will be described in greater detail below. Process diagrams are shown in FIGS. 1 and 2. The process of the invention can advantageously be applied to active ingredients which are insoluble or poorly soluble in water as defined in the European Pharmacopoeia Ed. 4$^{th}$, 2003, page 2891 and can be delivered to the lungs by inhalation in the form of aqueous suspensions. Preferred active ingredients are antibiotics and corticosteroids such as BDP and budesonide and its epimers, flunisolide, mometasone furoate, ciclesonide, rofleponide, triamcinolone acetonide and fluticasone propionate, useful for the treatment of respiratory diseases. In a particular embodiment, the active ingredients will give rise to hydrated forms which do not undergo crystalline regrowth in an aqueous suspension, such as flunisolide hemihydrate, amoxicillin and ampicillin trihydrate, cefaclor, cefadroxil and cephalexin monohydrate.

Preferred active ingredients are thermolabile corticosteroids. Even more preferably the active ingredient is beclomethasone dipropionate which, after crystallisation in the presence of water, gives rise to the monohydrated form.

BDP monohydrate can be characterised by X-ray diffractometry on the powders by exposure to Cu Kα radiation.

The angles (±0.1°/2φ) and relative intensities of the peaks (in brackets) are set out below (the intensity may change on variation of the powder packing conditions):

8.2 (85); 9.1 (13); 9.5 (12); 11.0 (21); 12.5 (39); 13.0 (13); 13.5 (6); 14.5 (100); 15.5 (20); 15.9 (20); 16.8 (25); 17.4 (16); 18.1 (22); 19.0 (23); 20.5 (11); 20.9 (9); 21.8 (19); 22.2 (14); 22.9 (18); 23.5 (11); 23.8 (18); 24.5 (13); 25.4 (14).

The monohydrate can be also characterised by means of its infrared (IR) spectrum. The principal absorption bands are reported below:

3560 cm$^{-1}$ (vs); 3510 (s); 3300 (vs); 1730 (vs); 1663 (s); 1630 (m); 1285 (m); 1190 (vs); 1120 (vs); 1090 (vs); 1053 (m); 973 (m); 940 (m) (vs=very strong; s=strong; m=average).

Finally, the monohydrate can be characterised by means of thermal analysis. After scanning from 50° C. to 350° C. at 15° C./min, the thermogram must show an endothermal peak between 100 and 140° C. (with the maximum at approx. 120° C.) corresponding to the loss of water of crystallisation followed by the melting endotherm of BDP at approx. 218° C.

Advantageously, the concentration of active ingredient in the final suspension is between 0.001 and 1% w/v, and preferably between 0.02 and 0.1% w/v. In the case of BDP monohydrate, the preferred concentration is 0.04% w/v.

The filtration through sterilizing filters requires prior dissolution of the active ingredient in an organic solvent in a reactor equipped with a stirring system (A in FIGS. 1 and 2). Various parameters must be evaluated in order choose the solvent with the most suitable properties: the solubility and stability of the active ingredient in said solvent, its miscibility with water, and the characteristics of toxicity, volatility and corrosiveness towards the walls of the apparatus. In general, the organic solvent must have a high solubilising capacity for the active ingredient, low toxicity and a low boiling point, must not be corrosive for the apparatus, must be able to form azeotropes with water with a high solvent content, and must preferably be miscible with water.

The solvent is advantageously selected from the group that comprises ethanol, acetone, methyl ethyl ketone and ethyl acetate. The solvent is preferably ethanol. Said solvents guarantee in particular a good solubility of corticosteroids, give solutions that are stable for at least two hours at 40° C., have a low boiling point (under 80° C.), are not corrosive, have low toxicity, and are miscible with water at the volume ratios used in the processes of this invention.

In the case of BDP, it has been found that when ethanol is used, the solid particles of BDP monohydrate immediately precipitate in crystalline form, whereas when acetone or ethyl acetate is used, BDP monohydrate first tends to separate in an amorphous, almost pitch-like form, which adheres to the walls of the container and then crumbles, subsequently giving a crystalline solid.

The type of filter employed to sterilise the solution will be chosen on the basis of the organic solvent used, and the porosity of said filter will necessarily be not more than 0.22 micron, preferably 0.2 micron, and even more preferably 0.1 micron. Nylon, Durapore or Teflon filters could advantageously be used. The preferred material is Nylon 66. The sterilizing filtration is preferably performed under pressure.

A turboemulsifier operating under vacuum, constituted by a steel container fitted with a jacket with a cavity wall suitable for steam heating and with a turbine and/or agitation system (B in FIGS. 1 and 2), could advantageously be used as the reactor in which the aqueous solution constituting the vehicle of the final formulation is prepared. The aqueous solution may contain the pharmaceutically acceptable ingredients commonly used for the preparation of aqueous suspensions, i.e. wetting agents such as polysorbate 20, polysorbate 80 or sorbitan monolaurate, isotonicity agents such as sodium chloride, and possibly stabilisers such as disodium edetate and/or buffer agents. The vehicle can be pre-sterilised by heat or filtration, preferably by heating at 121° C. for 20 minutes.

The active ingredient will be crystallised by adding the organic solution to the aqueous phase in a suitable reactor equipped with a stirring system and loading cells (C in FIGS. 1 and 2). The reactor can be fitted with an internal filter, as shown in FIG. 2.

In order to crystallise the active ingredient with the desired particle size distribution, the concentration of active ingredient in the organic solvent is advantageously between 2 and 30% w/v, and preferably between 5 and 25% w/v. The temperature of the solution, under supersaturated conditions, will be regulated so as to prevent recrystallisation of the active ingredient, and will preferably be between 25° C. and 80° C., more preferably between 40 and 70° C. The volume of the organic solution added will be much smaller than the aqueous solution constituting the vehicle, and the two solutions will preferably be in a ratio of between 0.001 and 0.02 v/v, and even more preferably between 0.005 and 0.01 v/v.

The time taken to add the organic solution to the aqueous solution will advantageously be between 1 and 20 minutes, and preferably between 2 and 10 minutes. The aqueous solution will preferably be maintained under stirring.

The temperature of the aqueous phase to which the organic solution is added will advantageously be maintained at between 5 and 50° C., and preferably between 10 and 25° C., for a time of between 5 minutes and 3 hours, preferably between 30 minutes and 2 hours, and even more preferably for a time less than or equal to 30 minutes.

In the case of BDP monohydrate, the best particle size distribution is obtained by operating at about 10° C.

In a preferred embodiment of the invention (FIG. 1), the aqueous solution will contain all the excipients. constituting the final formulation. In particular, it is preferable for wetting agents such as polysorbate 20, sorbitan monolaurate or their mixture to be present. This also allows rapid formation of the hydrated forms of particular active ingredients, even with relatively short addition times which are suitable for the formation of particles with a fine enough size. At the end of the crystallisation stage, the d(v,0.9) of the particles in suspension, i.e. the volumetric diameter below which 90% of the particles fall, will advantageously be less than or equal to 70, preferably 60, more preferably 50 micron, even more preferably less than or equal to 30 micron, as determined by laser diffraction (Malvern) after sonication; the d(v,0.5), i.e. the volumetric diameter below which 50% of the particles fall (MMAD), will be of about 20 micron, preferably equal to 10 micron, and the d(v,0.1), i.e. the volumetric diameter below which 10% of the particles fall, will be less than or equal to 4 micron.

In the process shown in FIG. 1, the organic solvent can be removed after addition of the organic solution to the aqueous vehicle by evaporation under vacuum and heating. Advantageously, the evaporation will be conducted at 40-60° C. for a time of between 30 minutes and 3 hours. If a reduction in water content is also observed during this operation, the suspension will be made up to volume so as to readjust the active ingredient assay.

Alternatively, the organic solvent can be removed by diafiltration. The suspension is circulated through a system of filters (E) installed in parallel to the reactor in which crystallisation takes place until the desired residual quantity of organic solvent is obtained; at the same time, the reactor is fed with pre-sterilised water to keep the volume, and therefore the assay of the active ingredient constant. This operation reduces the residual content of organic solvent to values less than or equal to 1000 ppm of the total weight of the formulation.

The wet micronization treatment is performed in a high-pressure homogenizer (H). By exploiting very high pressures, up to 1500 bar corresponding to 0.015 Pascal (1 bar equal to 10-5 Pascal), this apparatus reduces the size of the suspended particles and disperses them evenly by forced passage of fluid at high pressure and turbulence through a suitable valve. The extent to which the size of the suspended particles is reduced depends on the operating pressure and the shape and dimensions of the micronization chamber. Advantageously, the suspended particles will be treated at an operating pressure of between 100 and 1000 bar (0.001-0.01 Pascal) for one or more cycles of treatment, preferably between 150 and 800 bar (0.0015-0.008 Pascal); even more preferably, the particles will be treated at 600 bar (0.006 Pascal) for a single cycle of treatment.

This operation restricts the particle-size distribution curve so that the volumetric diameter of at least 90% of the suspended particles is less than or approximately equal to 10 micron, preferably of about 6 micron. Advantageously, the volumetric diameter of at least 50% of the suspended particles will be less than or approximately equal to 6 micron, and preferably of approximately 3 to 4 micron, and the volumetric diameter of at least 10% of the suspended particles will be less than or approximately equal to 2 micron. The particles obtained at the end of the crystallisation stage can also be isolated by filtration, dried and loaded into a fluid energy mill (D in FIG. 2). The filtration stage can take place either outside or inside reactor C. In the mill, a fluid, generally air or nitrogen, is injected at high pressure through nozzles in the bottom of the unit. The solid material is introduced into the fluid stream and, as a result of the high turbulence created, forces of friction and impact between the particles are generated.

Advantageously, the pressure of the fluid stream is lower than 12 bar, preferably is comprised between 5 and 6 bar. The preparation of the final formulation from the sterile micronised particles thus obtained is carried out under aseptic conditions, preferably according to the teaching of the International patent application no. WO 03/086347.

The micronised suspension is distributed, under aseptic conditions, in suitable containers constituted by multidose, or preferably monodose vials, which are pre-formed or made with the "blow, fill and seal" technology.

The invention is illustrated in greater detail in the example below.

EXAMPLES

Example 1

Preparation of a Sterile Aqueous Suspension Based on 0.04% (w/v) BDP Monohydrate Composition:

| Ingredients | Total quantity of the preparation | Quantity by unit dose |
| --- | --- | --- |
| Sterile micronised BDP monohydrate | 6 g | (0.8 mg) |
| Polysorbate (Tween) 20 | 15 g | (2.0 mg) |
| Sorbitan monolaurate | 3 g | (0.4 mg) |
| Sodium chloride | 135 g | (18.0 mg) |
| Water for injection q.s. for | 15 l | (2.0 ml) |

The first stage of preparation of the sterile suspension involves preparing a solution to be subjected to sterilisation by filtration. For this purpose, 6 g of BDP was dissolved at 55-60° C. in 60 ml of absolute ethanol (10% w/v). The solution was filtered under sterile conditions through an 0.2 μm Nylon 66 filter (Ø=5 cm) in approx. 1 min; the filter and filtration apparatus were washed with 10 ml of hot ethanol, which was combined with the rest. The organic solution, maintained under agitation, was dripped into 15 litres of aqueous vehicle containing the other ingredients of the formulation at 25° C. in approx. 10 min to give the ingredient in crystalline form in suspension. The organic solvent was eliminated by evaporation at 60° C. for one hour, operating under vacuum, and the suspension was made up to volume with water to readjust the titre of the active ingredient.

An aliquot of said suspension was filtered through an 0.45 µm filter; the solid obtained was washed thoroughly with water and dried at 40° C. under vacuum for 24 hours. The product obtained is constituted by BDP monohydrate, as confirmed by the Karl-Fischer test (% $H_2O$=3.2%, theoretical value 3.3%) and the calorimeter test. The size distribution of the particles in suspension was determined by laser diffraction (Malvern) after sonication. This type of analysis exploits the diffraction of a laser beam by the particles. The parameter considered is the median volumetric diameter in µm of 10%, 50% and 90% of the particles, expressed as d(v,0.1), d(v, 0.5) and d(v, 0.9) respectively, which is determined by assuming that the particles have a geometrical shape equivalent to a sphere. The result was as follows: d(v, 0.9)=50 micron, d(v, 0.5)=10 micron and d(v, 0.1)=1.8 micron.

After 2 hours the suspension obtained was micronised in a high-pressure Niro Soavi homogeniser at the pressure of 600 bar, for a single cycle of treatment.

The suspension obtained was analysed for particle size distribution with the Malvern technique after sonication. The assay and purity of the BDP in the formulation were determined by liquid chromatography (HPLC), and the residual ethanol content by headspace gas chromatography (HS-GC). The results are set out in Table 1.

TABLE 1

Chemical and physical parameters of the BDP aqueous suspension

| Description | Micronised suspension |
|---|---|
| Malvern | |
| d(v, 0.1), µm | 0.81 |
| d(v, 0.5), µm | 2.64 |
| d(v, 0.9), µm | 5.90 |
| Ethanol residue (HS-GC) | 0.1% w/w |
| BDP assay (HPLC) | 0.394 mg/ml |
| Total degradates (HPLC) | ≦0.5% |

The formulation prepared according to the process of the invention has the ideal particle distribution for pulmonary administration, with a residual ethanol content well lower than 2.5% w/w, the maximum tolerated limit in accordance with the International Conference on Harmonization (ICH) guideline Q 3 C "Impurities: residual solvents" issued in March 1998.

The particle size of the suspension was checked after 1 month of storage at a temperature below 7° C. No significant crystalline regrowth of the suspended particles was observed under these conditions.

The whole process can be performed under aseptic conditions.

Example 2

Preparation of an Aqueous Suspension Based on 0.05% (w/v) Budesonide

Composition

| Ingredients | Total quantity of the preparation | Quantity by unit dose |
|---|---|---|
| Sterile micronised budesonide | 2 g | (1.0 mg) |
| Polysorbate (Tween) 80 | 4 g | (2.0 mg) |
| Disodium edetate dihydrate | 2 g | (1.0 mg) |
| Sodium citrate dihydrate | 3.2 g | (1.6 mg) |
| Citric acid hydrate | 0.8 g | (0.4 mg) |
| Sodium chloride | 36 g | (18 mg) |
| Water for injection q.s. for | 4 l | (2.0 ml) |

Water (4 litres) was loaded in a 6 litres reactor. Sodium chloride (36.0 g) and Tween 80 (4.0 g) were added and the mixture was stirred for 5 minutes at 20-25° C. until dissolution was complete. Disodium edetate dihydrate (2.0 g), sodium citrate dihydrate (3.2 g) and citric acid hydrate (0.8 g) were added and the mixture was stirred for 5 minutes at 20-25° C.: the final pH was 5.25. Budesonide (2.0 g) was weighed in a 50 ml flask. Ethanol (16 ml) was added and the mixture was heated at 60-70° C. until dissolution was complete; the solution was transferred in a filter holder equipped with a nylon 0.2 µm filter.

Nitrogen pressure (0.8 bar) was gradually applied and the filtered solution was collected in a 50 ml dropping funnel. The solution was dropped in the 6 l reactor under vigorous stirring during 15 minutes, and immediate crystallization of budesonide was achieved. The filter and the dropping funnel were washed with ethanol (4 ml) which was dropped in the reactor. The so obtained suspension was stirred for 60 minutes at 20-25° C.

The crude suspension was gradually loaded in a Niro Soavi high-pressure homogenizer and micronized under the following conditions: $1^{st}$ cycle pressure: 150 bar; $2^{nd}$ cycle pressure: 600 bar. The collected micronized suspension was analysed in comparison to the suspension before has been subjected to the wet micronization treatment for the following analytical parameters: particle size distribution with the Malvern technique after sonication, budesonide assay, pH. The results are reported in Table 2

TABLE 2

Chemical and physical parameters of the budesonide aqueous suspension

| Description | Crude suspension | Micronised suspension |
|---|---|---|
| Malvern | | |
| d(v, 0.1), µm | 3.59 | 1.75 |
| d(v, 0.5), µm | 7.23 | 4.19 |
| d(v, 0.9), µm | 11.54 | 6.06 |
| pH | 5.25 | 5.35 |
| Budesonide asssay (HPLC) | — | 0.496 mg/ml |

The results show that the active ingredient has a good particle size distribution for pulmonary administration already after crystallisation by using as anti-solvent water and that it can be further improved by a wet micronization treatment in a high-pressure homogenizer.

The invention claimed is:

1. A process for the preparation of sterile formulations in the form of aqueous suspensions for pulmonary administration by inhalation comprising a micronised crystalline beclomethasone dipropionate monohydrate as an active ingredient, the process comprising:
   i) preparing a solution of the active ingredient in ethanol in a suitable reactor (A);
   ii) sterilizing the solution by filtration;
   iii) in parallel, preparing a sterile aqueous phase containing suitable excipients in a turboemulsifier (B) and transferring the sterile aqueous phase to a suitable reactor (C);
   iv) adding the sterile organic solution to the sterile aqueous phase in a manner suitable to provide the active ingredient in crystalline form in a suspension;
   v) eliminating the ethanol; and
   vi) subjecting the aqueous suspension to a wet micronization treatment in a high pressure homogenizer (H) to further reduce the particle size of the active ingredient;
   wherein:
   at least 90% of the suspended particles of the active ingredient have a particle size of 6 μm or less;
   the temperature of the sterile aqueous phase is maintained at a temperature of between 10 and 25° C. and
   wherein the angles (±0.1°/2Φ) and relative intensities of the peaks (in brackets) of said crystalline beclomethasone dipropionate monohydrate are set out below 8.2 (85); 9.1 (13); 9.5 (12); 11.0 (21); 12.5 (39); 13.0 (13); 13.5 (6); 14.5 (100); 15.5 (20); 15.9 (20); 16.8 (25); 17.4 (16); 18.1 (22); 19.0 (23); 20.5 (11); 20.9 (9); 21.8 (19); 22.2 (14); 22.9 (18); 23.5 (11); 23.8 (18); 24.5 (13); 25.4 (14).

2. The process as claimed in claim 1, wherein the organic solution is maintained at a temperature of between 25 and 80° C.

3. The process as claimed in claim 1, wherein the organic solution is added to the sterile aqueous phase over a period of between 1 and 20 minutes.

4. The process as claimed in claim 3, wherein the organic solution is added to the sterile aqueous phase over a period of between 2 and 10 minutes.

5. The process as claimed in claim 1, wherein the wet micronization treatment is performed at an operating pressure of between 100 and 1000 bar for one or more cycles of treatment.

6. The process as claimed in claim 5, wherein the wet micronization treatment is performed at an operating pressure of between 150 and 800 bar.

7. The process as claimed in claim 1, wherein the sterile aqueous phase comprises one or more pharmaceutically acceptable excipients selected from the group consisting of wetting agents, surfactants, viscosity-increasing agents, stabilising agents, isotonicity agents and buffers.

8. The process as claimed in claim 7, wherein the excipient comprises at least one wetting agent selected from the group consisting of polysorbate 20 and sorbitan monolaurate.

9. The process as claimed in claim 1, wherein the temperature of the sterile aqueous phase is maintained at a temperature of about 10° C.

10. A pharmaceutical formulation for pulmonary administration by inhalation, comprising:
    micronised solid particles of crystalline beclomethasone dipropionate monohydrate as an active ingredient suspended in a vehicle consisting of water and one or more pharmaceutically acceptable excipients;
    wherein:
    the one or more pharmaceutically acceptable excipients comprise at least one member selected from the group consisting of wetting agents, surfactants, isotonicity agents, stabilizers and buffers;
    at least 90% of the suspended particles have a particle size of 6 μm or less and
    wherein the angles (±0.1°/2Φ) and relative intensities of the peaks (in brackets) of said crystalline beclomethasone dipropionate monohydrate are set out below 8.2 (85); 9.1 (13); 9.5 (12); 11.0 (21); 12.5 (39); 13.0 (13); 13.5 (6); 14.5 (100); 15.5 (20); 15.9 (20); 16.8 (25); 17.4 (16); 18.1 (22); 19.0 (23); 20.5 (11); 20.9 (9); 21.8 (19); 22.2 (14); 22.9 (18); 23.5 (11); 23.8 (18); 24.5 (13); 25.4 (14).

11. The pharmaceutical formulation as claimed in claim 10, comprising a wetting agent, wherein the wetting agent is selected from the group consisting of polysorbate 20, polysorbate 80 and sorbitan monolaurate.

12. The pharmaceutical formulation as claimed in claim 10, comprising an isotonicity agent, wherein the isotonicity agent is sodium chloride.

13. The pharmaceutical formulation as claimed in claim 10, wherein a concentration of the active ingredient is 0.04% w/v.

14. A process for the preparation of sterile formulations in the form of aqueous suspensions for pulmonary administration by inhalation comprising a micronised crystalline beclomethasone dipropionate monohydrate as an active ingredient, the process consisting of:
    i) preparing a solution of the active ingredient in ethanol in a suitable reactor (A);
    ii) sterilizing the solution by filtration;
    iii) in parallel, preparing a sterile aqueous phase containing suitable excipients in a turboemulsifier (B) and transferring the sterile aqueous phase to a suitable reactor (C);
    iv) adding the sterile organic solution to the sterile aqueous phase in a manner suitable to provide the active ingredient in crystalline form in a suspension;
    v) eliminating the ethanol; and
    vi) subjecting the aqueous suspension to a wet micronization treatment in a high pressure homogenizer (H) to further reduce the particle size of the active ingredient;
    wherein:
    at least 90% of the suspended particles of the active ingredient have a particle size of 6 μm or less;
    the temperature of the sterile aqueous phase is maintained at a temperature of between 10 and 25° C. and
    wherein the angles (±0.1°/2Φ) and relative intensities of the peaks (in brackets) of said crystalline beclomethasone dipropionate monohydrate are set out below 8.2 (85); 9.1 (13); 9.5 (12); 11.0 (21); 12.5 (39); 13.0 (13); 13.5 (6); 14.5 (100); 15.5 (20); 15.9 (20); 16.8 (25); 17.4 (16); 18.1 (22); 19.0 (23); 20.5 (11); 20.9 (9); 21.8 (19); 22.2 (14); 22.9 (18); 23.5 (11); 23.8 (18); 24.5 (13); 25.4 (14).

* * * * *